United States Patent
Suzaki et al.

(10) Patent No.: US 10,422,728 B2
(45) Date of Patent: Sep. 24, 2019

(54) SAMPLE EXTRACTION KIT AND SAMPLE EXTRACTION METHOD

(71) Applicant: DENKA SEIKEN CO., LTD., Tokyo (JP)

(72) Inventors: Masashi Suzaki, Saitama (JP); Makoto Fukasawa, Saitama (JP); Yoshiaki Hirayama, Gosen (JP); Kazuhiro Akiishi, Gosen (JP)

(73) Assignee: Denka Seiken Co., Tokyo (JP)

( * ) Notice: Subject to any disclaimer, the term of this patent is extended or adjusted under 35 U.S.C. 154(b) by 369 days.

(21) Appl. No.: 15/513,298

(22) PCT Filed: Sep. 26, 2014

(86) PCT No.: PCT/JP2014/075672
§ 371 (c)(1),
(2) Date: Mar. 22, 2017

(87) PCT Pub. No.: WO2016/046966
PCT Pub. Date: Mar. 31, 2016

(65) Prior Publication Data
US 2017/0315028 A1  Nov. 2, 2017

(51) Int. Cl.
*G01N 1/28* (2006.01)
*G01N 1/10* (2006.01)
*G01N 33/48* (2006.01)
*B02C 19/00* (2006.01)
(Continued)

(52) U.S. Cl.
CPC ............ *G01N 1/286* (2013.01); *B01L 3/5029* (2013.01); *B02C 19/0006* (2013.01); *G01N 1/10* (2013.01); *G01N 1/28* (2013.01); *G01N 33/48* (2013.01); *B01L 3/505* (2013.01); *B01L 2300/0609* (2013.01); *B01L 2400/0481* (2013.01);
(Continued)

(58) Field of Classification Search
CPC ............ G01N 1/286; G01N 1/28; G01N 1/10; G01N 33/48; G01N 2001/2866; G01N 2001/028; B02C 19/0006; B01L 3/5029; B01L 2400/0481; B01L 2300/0609; B01L 3/505
See application file for complete search history.

(56) References Cited

U.S. PATENT DOCUMENTS

2006/0176767 A1  8/2006  Hlavinka et al.
2009/0084202 A1*  4/2009  Mimori .................. G01N 1/286
                                                                73/864.91

FOREIGN PATENT DOCUMENTS

| JP | 41-19083 | 9/1966 |
|----|----------|--------|
| JP | H0727686 | 1/1995 |
| JP | H10104139 | 4/1998 |

(Continued)

OTHER PUBLICATIONS

International Preliminary Report on Patentability issued in PCT/JP2014/075672 dated Mar. 28, 2017.

*Primary Examiner* — Dennis White
(74) *Attorney, Agent, or Firm* — Keller Jolley Preece

(57) ABSTRACT

A specimen extraction kit includes a flexible tubular container configured to contain an extraction liquid, two holding portions opposed to each other and arranged at opposite sides of the tubular container, a coupling portion that couples the opposing holding portions, and a bending rib arranged on each of the opposing holding portions and configured to bend the tubular container and an extraction subject.

15 Claims, 11 Drawing Sheets

(51) Int. Cl.
*B01L 3/00* (2006.01)
*G01N 1/02* (2006.01)
(52) U.S. Cl.
CPC .............. *G01N 2001/028* (2013.01); *G01N 2001/2866* (2013.01)

(56) References Cited

FOREIGN PATENT DOCUMENTS

| | | |
|---|---|---|
| JP | 2003-219972 | 8/2003 |
| JP | 2005-523746 | 8/2005 |
| JP | 2007-022652 | 2/2007 |
| JP | 2007-218903 | 8/2007 |
| JP | 2009-036732 | 2/2009 |
| JP | 2009-220065 | 10/2009 |
| JP | 2010-038640 | 2/2010 |
| JP | 2013-167509 | 8/2013 |
| JP | 2014-190904 | 10/2014 |
| WO | WO 2006-098297 | 9/2006 |
| WO | WO 2007-083617 | 7/2007 |
| WO | WO 2007-116837 | 10/2007 |

* cited by examiner

SAMPLE EXTRACTION KIT AND SAMPLE EXTRACTION METHOD

CROSS-REFERENCE TO RELATED APPLICATIONS

This application is a national phase entry under 35 U.S.C. § 371 of International Application No. PCT/JP2014/075672, filed Sep. 26, 2014. The entire contents of the foregoing patent application is hereby incorporated by reference.

TECHNICAL FIELD

The present invention relates to a specimen extraction kit that extracts a specimen in a flexible tubular container and to a method for extracting a specimen.

BACKGROUND ART

A tubular container is used to extract a specimen from an extraction subject that may contain a specimen or to which a specimen may be attached. In such a tubular container, it is desirable that many specimens be extracted from the extraction subject. Patent document 1 describes a method for extracting a specimen from an extraction subject in a tubular container by squeezing the extraction subject between fingers through the tubular container.

PRIOR ART DOCUMENT

Patent Document

Patent Document 1: Japanese Laid-Open Patent Publication No. 2007-218903

SUMMARY OF THE INVENTION

However, when just squeezing an extraction subject, the squeezing force may hardly act on the extraction subject in some cases.

It is an object of the present invention to provide a specimen extraction kit and a method for extracting a specimen that increase the specimen extraction efficiency.

A specimen extraction kit according to one embodiment of the present invention includes a flexible tubular container configured to contain an extraction liquid, an extraction subject accommodated in the tubular container, holding portions opposed to each other and arranged at opposite sides of a circumferential wall of the tubular container, an elastically deformable coupling portion that couples the holding portions, and a bending portion arranged on each of the holding portions. The bending portion is configured to bend the tubular container and the extraction subject.

In this structure, the tubular container and the extraction subject are bent by the bending portion with the extraction subject accommodated in the tubular container. As a result, as compared to an extraction aspect in which the extraction subject is just squeezed between fingers or the like, the deformation degree of the extraction subject is increased. Thus, the extraction subject efficiency is increased.

The specimen extraction may further include a squeezing portion arranged on the opposing holding portions. The squeezing portion squeezes the bent tubular container and the extraction subject.

In this structure, since the bent extraction subject is further squeezed, specimens are further easily squeezed from the deformed extraction subject. As a result, as compared to an extraction aspect in which the extraction member is just bent, the extraction subject efficiency is increased.

In one example, the bending portion is a projection that projects from each of the opposing holding portions to another one of the holding portions, and the projection bends and squeezes the tubular container and the extraction subject.

In this structure, the projection that projects from each of the opposing holding portions functions to bend the extraction subject and squeeze the extraction subject. Thus, as compared to a structure in which the two functions are performed by different portions, the structure of the specimen extraction kit is easily formed.

In one example, the projections arranged on the opposing holding portions are located at different positions in a direction in which the tubular container extends, and the projections bend and squeeze the tubular container and the extraction subject when the opposing holding portions are moved toward each other.

In this structure, when the opposing holding portions are moved to each other, the projection that projects from each holding portion bends and squeezes the tubular container. Thus, as compared to an extraction process in which the bending of the extraction subject and the squeezing of the extraction subject are performed separately, the steps necessary to extract specimens are simplified.

In one example, the tubular container includes a portion that is gradually tapered toward a lower end, and the tubular container is bent and squeezed below a middle of the tubular container in the direction in which the tubular container extends.

In this structure, the tubular container including the portion that is gradually tapered toward the lower end is bent at the lower side of the tubular container. Thus, as compared to a structure in which the tubular container is bent at the upper side of the tubular container, the load on a user necessary to bend the tubular container is decreased.

A method for extracting a specimen according to one aspect of the present invention includes holding a flexible tubular container, which is configured to contain an extraction liquid, and an extraction subject, which is accommodated in the tubular container, with opposing holding portions to bend the tubular container and the extraction subject and extract a specimen from the extraction subject.

Other aspects and advantages will become apparent from the following description and the accompanying drawings that illustrate the examples of the technical ideas according to the present invention.

EMBODIMENTS OF THE INVENTION

Figure 1:
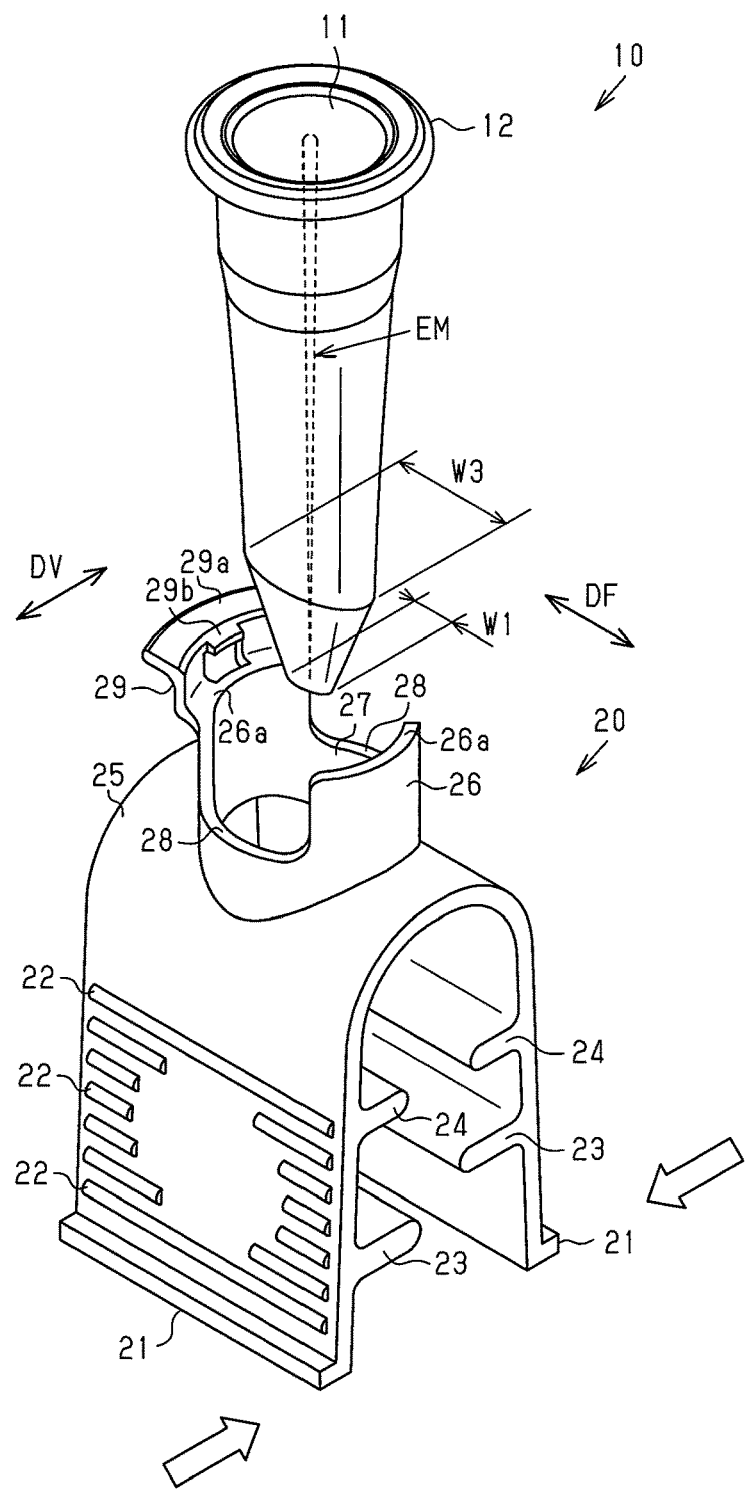
FIG. 1 is a perspective view showing a specimen extraction kit according to one embodiment of the present invention with a tubular container separated from a holding member.

While various modifications and alternative forms are acceptable for the present invention, particular embodiments are shown in the drawings as examples and will be described below in detail. However, the present invention is not limited to the described particular embodiments. Rather, the present invention is intended to cover all modifications, equivalents, and alternatives that are within the scope of the present invention defined by the accompanying claims.

A specimen extraction kit according to one embodiment of the present invention will now be described.

Structure of Specimen Extraction Kit

As shown in FIG. 1, a specimen extraction kit includes a tubular container 10 configured to contain an extraction liquid, a holding member 20 that assists the extraction of specimens, and an extraction subject EM. The extraction subject EM only needs to be a member that is immersed in an extraction liquid in the tubular container 10 to elute a specimen. The extraction subject EM is, for example, a paper point, a swab, a hair implantation swab, a sponge, paper, or nonwoven fabric.

The tubular container 10 is a flexible tube that includes an open upper end and a closed lower end. The tubular container 10 includes a portion that is gradually tapered toward the lower end and shaped to have an elliptic form stretched out in a major axis direction DF. The upper end of the tubular container 10 includes a container opening 11, which is a circular hole. A flange 12 extends around the entire circumference of the tubular container 10 and surrounds the container opening 11. The lower end of the tubular container 10 has a width in the major axis direction DF that is referred to as the first container width W1 and a width in a direction orthogonal to the major axis direction DF that is referred to as the second container width W2 (refer to FIG. 4). Further, the upper end of the portion of the tubular container 10 that is gradually tapered toward the lower end has a width in the major axis direction DF that is referred to as the third container width W3. The thickness of the tubular container 10 is referred to as the container thickness T. The extraction subject EM has a width in a minor axis direction DV between two bending ribs 23 that is referred to as the extraction subject thickness P.

The tubular container 10 only needs to be formed from a flexible resin, for example, polyethylene, polypropylene, polyethylene terephthalate, polyvinyl chloride, or silicone rubber. The tubular container 10 may be transparent or translucent. However, it is preferred that the tubular container 10 be transparent or translucent so that a user can see where the extraction subject EM is located and the elution of specimens into the extraction liquid. Further, the upper end of the tubular container 10 may include a nozzle that discharges the extraction liquid out of the tubular container 10.

The holding member 20 may be a bent plate member having a reverse U-shaped cross section in a side view. The holding member 20 is formed from, for example, polyethylene, polypropylene, ABS resin, polystyrene, AS resin, polycarbonate, polyethylene terephthalate, polyvinyl chloride, or spring steel. The holding member 20 has, for example, a reverse U-shaped form. The holding member 20 includes a coupling portion, which is, for example, a curved or bending portion, and two holding portions 21. The two holding portions 21 extend from the coupling portion toward the two free ends, which are located distant from the coupling portion. The two holding portions 21 may be flat plates opposing each other. The outer surfaces of the two holding portions 21 may be symmetrical with each other with respect to a plane extending in the axis or the extending direction of the holding member 20 or the tubular container 10. The outer surface of each holding portion 21 may be roughened and, for example, include anti-slip ribs 22 that are orthogonal to the extending direction of the holding portion 21.

The inner surface of each of the two holding portions 21 includes the bending ribs 23 serving as projections that project inwardly. Guide ribs 24 are arranged at positions that differ from where the bending ribs 23 are located (for example, upper sides of bending ribs 23). The guide ribs 24 project inwardly from the inner surfaces of the holding portions 21. Each bending rib 23 and each guide rib 24 extend in the major axis direction DF over the entire corresponding holding portion 21.

Each holding portion 21 includes an upper end coupled to a plate spring 25 that is bent and upwardly bulged. The plate spring 25, which serves as a coupling portion, is coupled to the holding portions 21 entirely in a direction orthogonal to the extending direction. The two holding portions 21 are molded integrally with the plate spring 25. When the distal ends of the two holding portions 21 are, for example, held between fingers and receive external force that moves the distal ends toward each other as shown by the arrows in FIG. 1, the plate spring 25 elastically deforms and decreases the radius of curvature of the plate spring 25. As a result, the two holding portions 21 are moved toward each other. The two holding portions 21 are moved and pivoted about the plate spring 25. The distal ends of the two holding portions 21 are particularly close to each other. The distance between the two holding portions 21 gradually increases from the basal ends of the holding portions 21 toward the distal ends of the holding portions 21.

The outer surface of the plate spring 25 includes a circular insertion tube 26 extending upwardly from the plate spring 25. The insertion tube 26 includes a circular insertion hole 27 that extends through the plate spring 25 and is in communication with the gap between the two holding portions 21. The size of the insertion hole 27 is set to allow the tubular container 10 to be inserted into and removed from the insertion hole 27. The inner diameter of the insertion hole 27 is substantially equal to the inner diameter of the flange 12 and is smaller than the outer diameter of the flange 12. The insertion tube 26 includes a circumferential wall including two slots 28 extending in the extending direction. The two slots 28 are extended along substantially the entire insertion tubes 26 in the extending direction and located at opposing positions. The size of each slot 28 is, for example, substantially equal to the size of a fingertip of a user. The insertion hole 27 is one example of a container receiving port.

The insertion tube 26 includes an upper end including a restriction portion 29. Only one of two portions of the upper end of the insertion tube 26 that are located between the two slots 28 includes the restriction portion 29. The restriction portion 29 extends from an upper end surface 26a of the insertion tube 26 and is increased in diameter. The restriction portion 29 is an arcuate surface formed by continuously extending an arc, which has a larger inner diameter than the insertion tube 26, toward the upper side. The restriction portion 29 includes an upper end including an operation piece 29a extending toward the radially outer side of the insertion tube 26 and an engagement tab 29b extending toward the radially inner side of the insertion tube 26.

Figure 2:
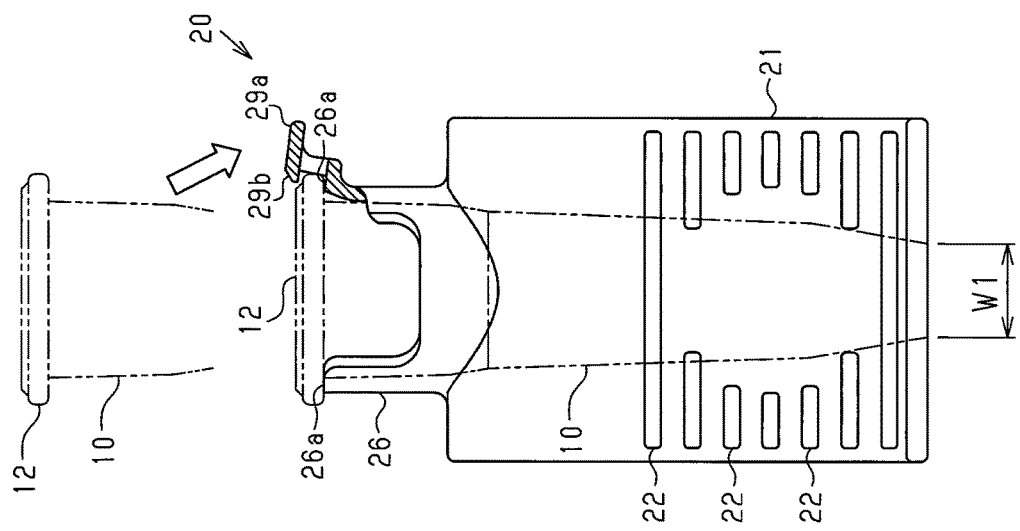
FIG. 2 is a partially cutaway front view showing the holding member.

As shown in FIG. 2, the inner diameter Di of the restriction portion 29, which has the form of an arcuate surface, is substantially equal to the outer diameter of the flange 12 of the tubular container 10. When the inner surface of the restriction portion 29 opposes an outer circumferential surface of the flange 12, the upper end surface 26a of the insertion tube 26 restricts downward movement of the flange 12, and the engagement tab 29b of the restriction portion 29 restricts upward movement of the flange 12.

Figure 3:
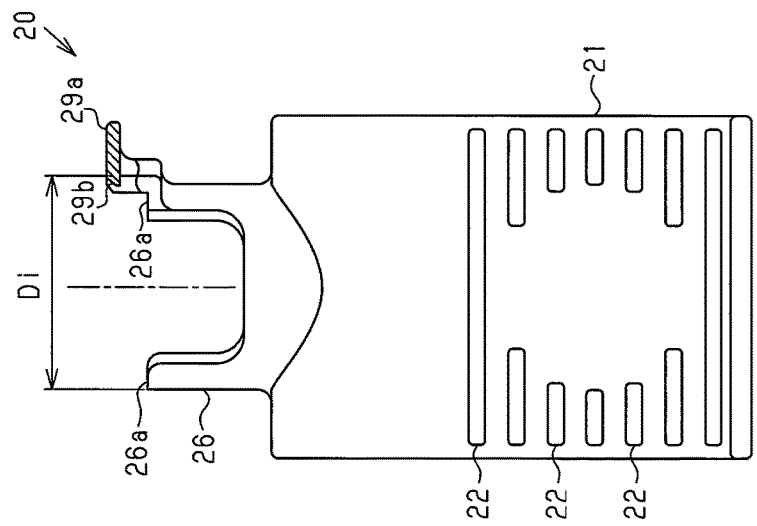
FIG. 3 is a schematic view showing a process for fixing the tubular container to the holding member.

As shown by the arrow in FIG. 3, when downward force that acts toward the radially outer side of the insertion tube 26 is applied to the operation piece 29a of the restriction portion 29, substantially the entire restriction portion 29 including the engagement tab 29b is elastically deformed. This downwardly flexes substantially the entire restriction portion 29 toward the radially outer side. Then, in the state in which the restriction portion 29 is flexed, the tubular container 10 is inserted into the insertion hole 27. This abuts the lower surface of the flange 12 against the upper end surface 26a of the insertion tube 26. Subsequently, in the state in which the lower surface of the flange 12 is abut against the upper end surface 26a of the insertion tube 26, the force applied to the operation piece 29a is released. This cancels the elastic deformation of the restriction portion 29, and the engagement tab 29b partially covers the upper surface of the flange 12. In this manner, the engagement of the flange 12 and the restriction portion 29 restricts movement of the tubular container 10 in the extending direction of the tubular container 10.

In the state in which the flange 12 is engaged with the restriction portion 29, when the downward force that acts toward the radially outer side is applied to the operation piece 29a again, substantially the entire restriction portion 29 including the engagement tab 29b is elastically deformed. This downwardly flexes substantially the entire restriction portion 29 toward the radially outer side and cancels the movement restriction of the tubular container 10 in the extending direction of the tubular container 10. As a result, the tubular container 10 is allowed to be inserted into and removed from the insertion tube 26. The two portions of the upper end of the insertion tube 26 that are located between the two slots 28 may each include the restriction portion 29. Alternatively, regardless of the number of the slots 28, the upper end of the insertion tube 26 may include two or more restriction portions 29.

Figure 4:
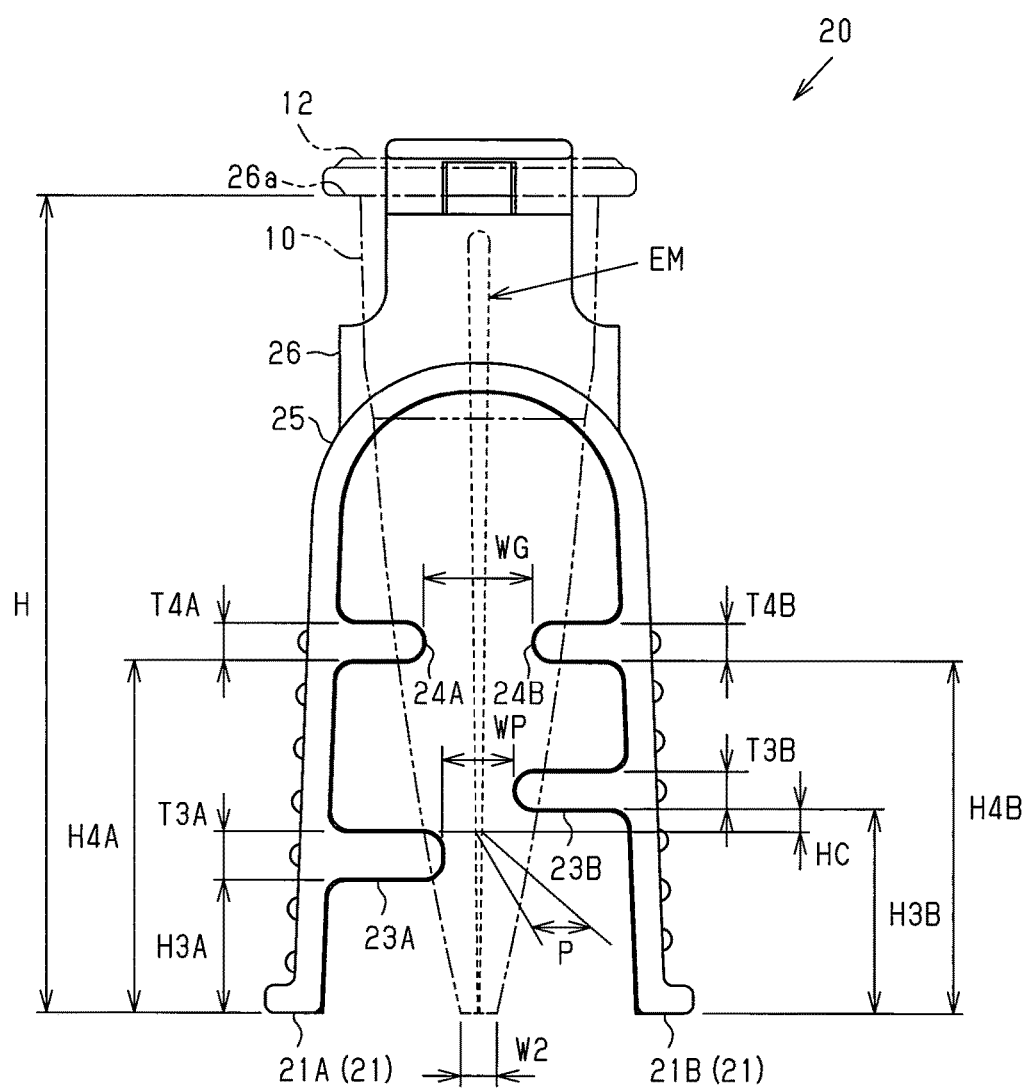
FIG. 4 is a side view of the holding member showing the relationship of the tubular container and the holding member.

As shown in FIG. 4, a first bending rib 23A and a first guide rib 24A project from the inner surface of a first holding portion 21A, which is one of the two holding portions 21, toward a second holding portion 21B, which is the other one of the two holding portions 21. A second bending rib 23B and a second guide rib 24B project from the inner surface of the second holding portion 21B toward the first holding portion 21A. The direction in which the two holding portions 21 oppose each other is referred to as the holding direction. In the present embodiment, the first bending rib 23A and the second bending rib 23B each function as a projection serving as a bending portion and a squeezing portion.

In the first holding portion 21A, the distance in the extending direction between a distal end of the first holding portion 21A and the upper end surface 26a of the insertion tube 26 is referred to as the container height H, which is the length of the tubular container 10 in the extending direction. Further, the distance in the extending direction between the distal end of the first holding portion 21A and the first bending rib 23A is referred to as the first bending rib height H3A, and the distance in the extending direction between the distal end of the first holding portion 21A and the first guide rib 24A is referred to as the first guide rib height H4A. In addition, the thickness of the first bending rib 23A in the extending direction is referred to as the first bending rib thickness T3A, and the thickness of the first guide rib 24A in the extending direction is referred to as the first guide rib thickness T4A.

In the second holding portion 21B, the distance in the extending direction between the distal end of the second holding portion 21B and the second bending rib 23B is referred to as the second bending rib height H3B, and the distance in the extending direction between the distal end of the second holding portion 21B and the second guide rib 24B is referred to as the second guide rib height H4B. In addition, the thickness of the second bending rib 23B in the extending direction is referred to as the second bending rib thickness T3B, and the thickness of the second guide rib 24B in the extending direction is referred to as the second guide rib thickness T4B.

The distance in the extending direction between the first bending rib 23A and the second bending rib 23B is referred to as the bending width HC. The distance in the holding direction between a distal end of the first bending rib 23A and a distal end of the second bending rib 23B is referred to as the holding width WP. The distance in the holding direction between a distal end of the first guide rib 24A and a distal end of the second guide rib 24B is referred to as the guide width WG.

The first bending rib 23A and the second bending rib 23B are located at different positions in the extending direction. The second bending rib height H3B is greater than the first bending rib height H3A. It is preferred that the first bending rib height H3A and the second bending rib height H3B satisfy the following expression 1 with respect to the container height H so that the tubular container 10 easily bends and increases the specimen extraction efficiency.

$$H3A+T3A<H3B<H3B+T3B<H/2 \qquad \text{(expression 1)}$$

Even when the first bending rib height H3A is 0 mm, the tubular container 10 is bendable. However, it is particularly preferred that the first bending rib height H3A and the second bending rib height H3B satisfy the following expression 2 so that the first bending rib 23A and the second bending rib 23B bend the extraction subject EM and further squeeze the extraction subject EM to increase the specimen extraction efficiency.

$$HC=H3B-(H3A+T3A) \leq 2T+P \quad \text{(expression 2)}$$

The first guide rib 24A and the second guide rib 24B are located at opposing positions. The first guide rib height H4A is substantially equal to the second guide rib height H4B. It is preferred that the first guide rib thickness T4A be equal to the second guide rib thickness T4B so that the position of the tubular container 10 relative to the holding member 20 does not vary each time the tubular container 10 is received. Further, it is preferred that the guide width WG satisfy the following expression 3 with respect to the first container width W1, the second container width W2, and the third container width W3 of the tubular container 10.

$$W2<WG<W3, W1<W3 \quad \text{(expression 3)}$$

It is preferred that the holding width WP satisfy the following expression 4 with respect to the guide width WG and the second container width W2 to allow the tubular container 10 to be smoothly inserted into the holding member 20.

$$W2<WP<WG \quad \text{(expression 4)}$$

Operation of Specimen Extraction Kit

The operation of the specimen extraction kit based on the specimen extraction method using the specimen extraction kit will now be described.

Figure 5:
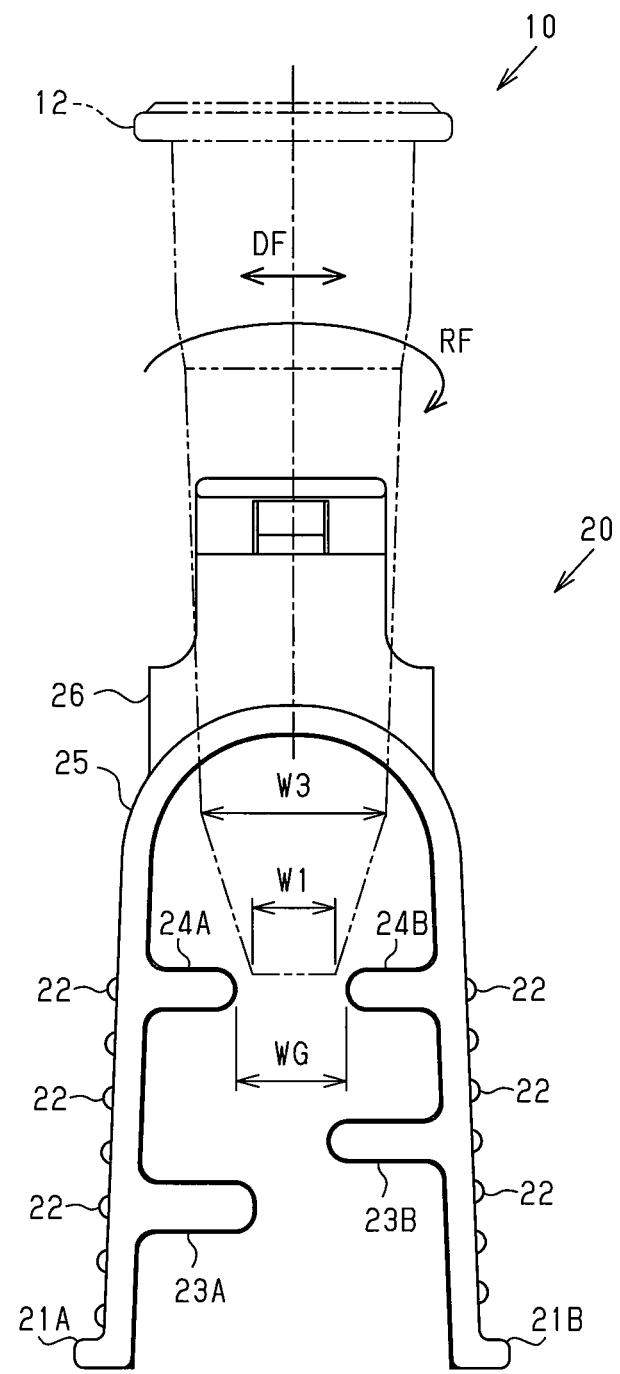
FIG. 5 is a schematic view showing a process for fixing the tubular container to the holding member.

As shown in FIG. 5, when the tubular container 10 is inserted from the upper side of the two holding portions 21A and 21B into the space between the two holding portions 21A and 21B, the lower end of the tubular container 10 passes through the gap between the two guide ribs 24A and 24B. In this case, as long as the above expression 3 is satisfied, the tubular container 10 is inserted into the gap between the two guide ribs 24A and 24B with the major axis direction DF of the tubular container 10 substantially coinciding with the holding direction of the guide ribs 24A and 24B. Then, the portion of the tubular container 10 that is gradually tapered toward the lower end is inserted between the two guide ribs 24A and 24B.

When the direction orthogonal to the major axis direction DF is referred to as the minor axis direction DV, the guide width WG of the gap between the two guide ribs 24A and 24B is greater than the second container width W2 of the lower end of the tubular container 10 in the minor axis direction DV and the tubular container 10 is gradually tapered toward the lower side of the tubular container 10. Thus, when force is applied to the tubular container 10 to further insert the tubular container 10, the tubular container 10 is rotated about its axis (single-dashed line) as shown by the arrow RF in FIG. 5 so that the major axis direction DF of the tubular container 10 intersects the holding direction of the guide ribs 24A and 24B.

Figure 6:
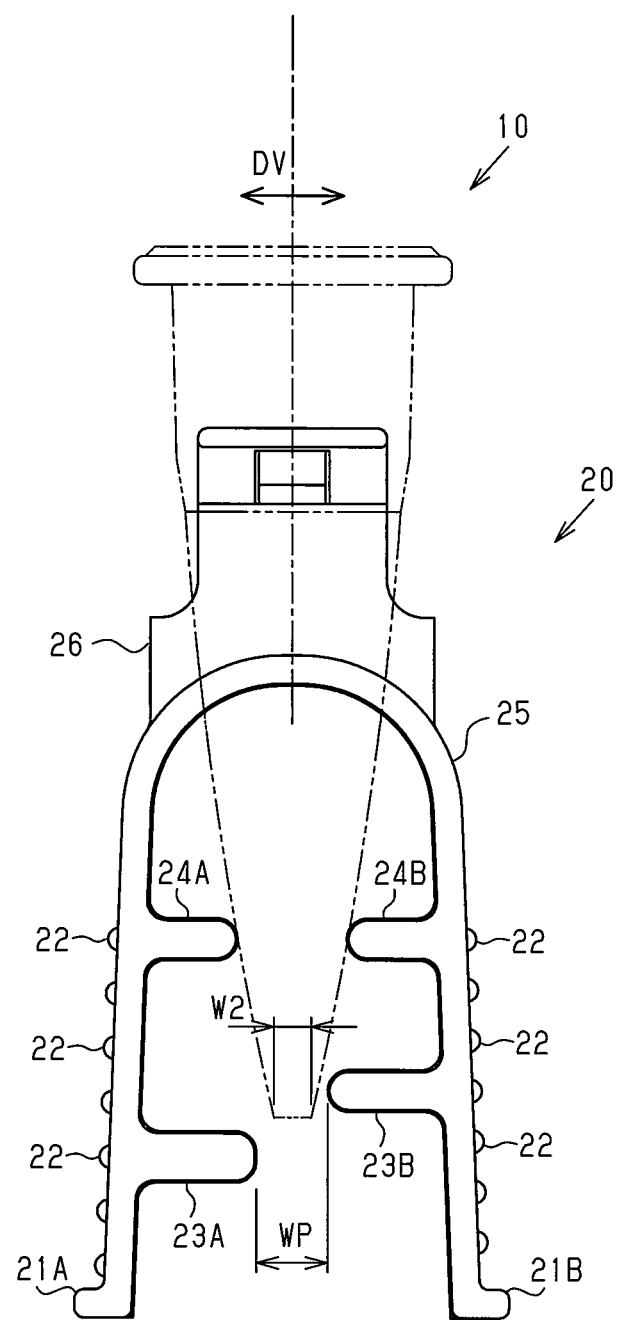
FIG. 6 is a schematic view showing a process for fixing the tubular container to the holding member.

As shown in FIG. 6, after the tubular container 10 is rotated about its axis, the tubular container 10 is continuously inserted into the gap between the two guide ribs 24A and 24B with the minor axis direction DV of the tubular container 10 substantially coinciding with the holding direction of the two guide ribs 24A and 24B. In this case, as long as the above expression 3 is satisfied, the holding width WP of the gap between the two bending ribs 23A and 23B is greater than the second container width W2 in the minor axis direction. Thus, the lower end of the tubular container 10 that has passed through the gap between the two guide ribs 24A and 24B smoothly passes through the gap between the two bending ribs 23A and 23B with the minor axis direction DV coinciding with the holding direction. As a result, the tubular container 10 is located in the gap between the two holding portions 21 with the flattened surfaces of the tubular container 10 opposing the guide ribs 24A and 24B and the flattened surfaces of the tubular container 10 opposing the bending ribs 23A and 23B.

The tubular container 10 is not rotated when the tubular container 10 is inserted into the gap between the two guide ribs 24A and 24B with the major axis direction DF of the tubular container 10 orthogonal to the holding direction. This arranges the tubular container 10 in the gap between the two holding portions 21 with the flattened surfaces of the tubular container 10 opposing the guide ribs 24A and 24B.

Thus, the position of the tubular container 10 relative to the two holding portions 21 is always the same in the circumferential direction of the tubular container 10 each time the tubular container 10 is inserted into the holding member 20. This reduces differences in the extraction results that would be caused by differences in the position of the tubular container 10 relative to the two holding portions 21 each time the tubular container 10 is inserted into the holding member 20.

Figure 7:
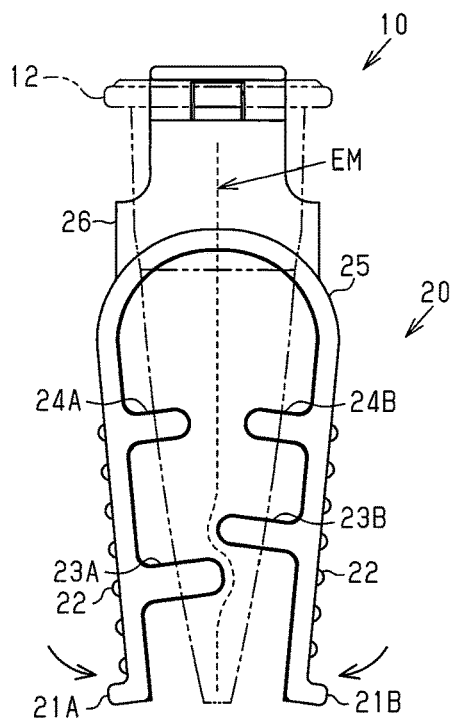
FIG. 7 is a schematic view showing the narrowing of a gap between two holding portions.

As shown in FIG. 7, in the state in which the tubular container 10 is located in the gap between the two holding portions 21, the two holding portions 21 are, for example, held between fingers that apply external force in the direction in which the two holding portions 21 are moved toward each other. This elastically deforms the plate spring 25, decreases the curvature of the plate spring 25, and moves the two holding portions 21 toward each other. The distal ends of the two holding portions 21 are particularly close to each other, and the distance between the two holding portions 21 gradually increases from the basal ends toward the distal ends of the holding portions 21. Thus, as long as expression 4 is satisfied, the gap between the two bending ribs 23A and 23B is smaller than the gap between the two guide ribs 24A and 24B.

Figure 8:
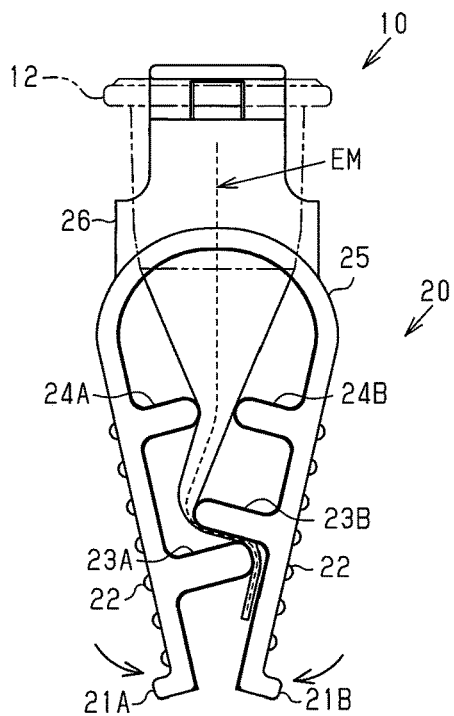
FIG. 8 is a schematic view showing the bending of the tubular container when the gap between the two holding portions is narrowed.

As shown in FIG. 8, as the two holding portions 21 are further moved toward each other, the two bending ribs 23A and 23B press and bend the tubular container 10. Further, the extraction subject EM accommodated in the tubular container 10 is bent in accordance with the bending of the tubular container 10 and squeezed by the distal end of the first bending rib 23A. As a result, as compared to a structure that does not bend the tubular container 10 and just squeezes the extraction subject EM between the fingers or the like, the deformation degree of extraction subject EM is increased. Further, since specimens are squeezed out of the extraction subject EM into the extraction liquid, the subject extraction efficiency is increased.

Further, when just squeezing the extraction subject EM between fingers, the squeezing degree of the extraction subject EM greatly differs depending on the finger size of the user and the force applied by the user. Thus, the specimen extraction efficiency differs depending on the skill of the user. When the squeezing degree of the extraction subject EM is maintained by pressure of a mechanical pressurizer, generally the same specimen extraction efficiency is maintained for each extraction subject EM. However, a drive source that drives the pressurizer and a controller that controls the drive amount of the pressurizer are required to extract specimens from the extraction subject EM. Thus, the user needs to prepare such a drive source and controller.

In this regard, when the holding member 20 is used to bend the tubular container 10, the fulcrum that bends the tubular container 10 and the working point are the two bending ribs 23. This increases the specimen extraction efficiency and reduces differences in the specimen extraction efficiency that are caused by differences in the skill of the user. In addition, the position of the tubular container 10 in the extending direction is set relative to the holding member 20 by the engagement of the flange 12 and the insertion tube 26. Further, two guide ribs 24A and 24B guide the tubular container 10 to set the circumferential position of the tubular container 10 relative to the holding member 20. This further reduces differences in the specimen extraction efficiency caused by differences in the skill of the user.

As long as expression 1 is satisfied, the tubular container 10 that is gradually tapered toward the lower side is bent at the lower side of the tubular container 10. This reduces the load on the user that would be required to bend the tubular container 10 as compared to when the tubular container 10 is bent at the upper side of the tubular container 10.

As long as expression 2 is satisfied, when the two holding portions 21 are moved toward each other, the distal end of the first bending rib 23A bends and squeezes the tubular container 10 in the gap between the two bending ribs 23A and 23B. This also bends and squeezes the extraction subject EM, which is held by the inner surface of the tubular container 10, toward the inner surface of the tubular container 10. Thus, the specimen extraction efficiency is further increased as compared to when the extraction subject EM is just bent.

EXAMPLE

An example related to the specimen extraction efficiency will now be described.

Two paper points (length of 30 mm) absorbed 4 μL of a bacterial liquid having a constant concentration. Then, the two paper points were accommodated in the tubular container 10 (length of 44 mm) and immersed in 400 μL of an extraction liquid contained in the tubular container 10. Then, after performing an extraction process on the paper points, 50 μL of an extraction liquid, which had undergone the extraction process, was applied to a test device. After fifteen minutes, the line strength, which is a specimen concentration index, was measured to obtain the line strength of the example, that is, the sensitivity. The line strength was measured by setting the specimens in the bacterial liquid to 1.0. The size of each element of the tubular container 10 and the size of each element of the holding member 20 are listed below as extraction conditions.

Further, the line strength of a comparative example was obtained without using the holding member 20 by rubbing the tubular container 10, in which the paper points were immersed, with hands twenty times.

Extraction Condition
Number of Extractions (Number of Bending): 20
Holding Members
Material: Polystyrene
First Bending Rib Height H3A: 7.25 mm
Second Bending Rib Height H3B: 11.0 mm
First Bending Rib Thickness T3A: 2.5 mm
First Guide Rib Height H4A: 19.0 mm
Second Guide Rib Height H4B: 19.0 mm
General Thickness (Thickness except Rib): 1.5 mm
Bending Modulus of Plate Spring 25: 2500 MPa
Bending Width HC: 1.25 mm
Guide Width WG: 6.0 mm
Holding Width WP: 4.0 mm
Container
Material: Polyethylene
Container Height H: 44.0 mm
Container Thickness T: 0.6 mm
Height of Extraction Liquid: 20.0 mm
First Container Width W1: 4.0 mm
Second Container Width W1: 2.0 mm
Third Container Width W1: 8.0 mm
Extraction subject Thickness P: 0.8 mm When hand-rubbing was performed in the prior art, the sensitivity was 0.35. When the holding member 20 is used, the sensitivity was 0.80. This confirms that the above specimen extraction kit increased the specimen extraction efficiency.

EXPERIMENTAL EXAMPLES

The relationship of each of the elements of the specimen extraction kit and the specimen extraction efficiency will now be described based on the result of a regression analysis.

In order to specify factors (explanatory variables) that illustrate the sensitivity, or line strength, first to fifth explanatory variables (described below) were used under the same conditions as the example except for the explanatory variables to obtain the line strengths of eighty-four experimental examples. The data obtained from the eighty-four experimental examples was used to perform a regression analysis. Table 1 shows the multiple regression coefficient and the p-value of each of the factors that were obtained through the multiple regression analysis. The p-value is a term that is generally used for statistics such as F-test and t-test. When the p-value is less than 0.01, the p-value is highly significant and has a significant level of 1% (multiple regression equations are fitted with a probability of 99%).

First Explanatory Variable: Number of Extractions

The number of times the tubular container 10 was rubbed with hands, that is, the number of times the tubular container 10 was bent with the holding member 20, was changed to 5, 10, 20, and 30 and used as the first explanatory variable.

Second Explanatory Variable: Second Bending Rib Height H3B

The second bending rib height H3B was changed to 7 mm, 9 mm, 11 mm, and 13 mm and used as the second explanatory variable.

Third Explanatory Variable: General Thickness

The thickness of the portion of the holding member 20 excluding the bending ribs 23A and 23B and the guide ribs 24A and 24B was changed to 1.0 mm and 1.5 mm and used as the third explanatory variable.

Fourth Explanatory Variable: First Bending Rib Thickness T3A

The first bending rib thickness T3A was changed to 2.0 mm and 2.5 mm and used as the fourth explanatory variable.

Fifth Explanatory Variable: Bending Modulus of Plate Spring 25

The bending modulus of the plate spring 25 was changed to 800 MPa, 1200 MPa, 1600 MPa, and 2500 MPa and used as the fifth explanatory variable.

The sensitivity was 0.70 in an experimental example in which the number of extractions was 10, the second bending rib height H3B was 11 mm, the general thickness was 1.5 mm, the first bending rib thickness T3A was 2.0 mm, and the bending modulus of the plate spring 25 was 2500 MPa.

The sensitivity was 0.80 in an experimental example in which the number of extractions was 10, the second bending rib height H3B was 11 mm, the general thickness was 1.5 mm, the first bending rib thickness T3A was 2.5 mm, and the bending modulus of the plate spring 25 was 2500 MPa.

The sensitivity was 0.75 in an experimental example in which the number of extractions was 10, the second bending rib height H3B was 11 mm, the general thickness was 1.5 mm, the first bending rib thickness T3A was 2.5 mm, and the bending modulus of the plate spring 25 was 800 MPa.

The sensitivity was 0.80 in an experimental example in which the number of extractions was 10, the second bending rib height H3B was 11 mm, the general thickness was 1.0 mm, the first bending rib thickness T3A was 2.0 mm, and the bending modulus of the plate spring 25 was 2500 MPa.

The sensitivity was 0.80 in an experimental example in which the number of extracting was 20, the second bending rib height H3B was 11 mm, the general thickness was 1.5 mm, the first bending rib thickness T3A was 2.0 mm, and the bending modulus of the plate spring 25 was 2500 MPa.

TABLE 1

| | | |
|---|---|---|
| Multiple Correlation Coefficient R | | 0.864410706 |
| Determination Coefficient R2 | | 0.747205869 |
| Number of Observations | | 84 |

| | Regression Coefficient | Standard Error |
|---|---|---|
| Intercept | −0.212894024 | 0.163155961 |
| First Explanatory Variable | 0.004181129 | 0.000987747 |
| Second Explanatory Variable | 0.062555886 | 0.005022683 |
| Third Explanatory Variable | −0.176623907 | 0.077427308 |
| Fourth Explanatory Variable | 0.170007357 | 0.039652925 |
| Fifth Explanatory Variable | 3.44975E−05 | 1.62676E−05 |

| | P-value | t-value |
|---|---|---|
| Intercept | 0.195780592 | −1.304849809 |
| First Explanatory Variable | 6.24077E−05 | 4.232996444 |
| Second Explanatory Variable | 3.1364E−20 | 12.45467605 |
| Third Explanatory Variable | 0.025267751 | −2.2811578 |
| Fourth Explanatory Variable | 5.12375E−05 | 4.287385074 |
| Fifth Explanatory Variable | 0.037131336 | 2.120623387 |

As shown in Table 1, when the regression coefficient of each of the explanatory variables was obtained, the multiple correlation coefficient R was 0.8644, which is significantly close to 1, and the determination coefficient R square value was 0.7472. Thus, the regression equation of the multiple regression analysis was fitted in a preferred manner. Among the first to fifth explanatory variables, the second explanatory variable (second bending rib height H3B) had a regression coefficient of 0.0626 and the p-value for the regression coefficient was $3.1364 \times 10E-20$ (<0.01), which is the smallest value. This confirms that the second bending rib height H3B highly affected the sensitivity with a significant level of 1%.

Figure 9:
FIG. 9 is a chart showing the result of an experimental example of the relationship of the second bending rib height and the sensitivity.

As shown in FIG. 9, the predicted value of sensitivity increases as the second bending rib height H3B increases. The predicted value of sensitivity is generally saturated at a range in which the second bending rib height H3B is greater than or equal to 11 mm. In other words, it is preferred that the second bending rib height H3B be set to a range in which the container height H (44.0 mm) is less than or equal to 50%, and it is further preferred that the second bending rib height H3B be set to a range in which the container height H is greater than or equal to 20.0% and less than or equal to 35.0%. Further, it is preferred that the second bending rib height H3B be set to a range in which the height of an extraction liquid (20.0 mm) is less than or equal to 75%, and it is further preferred that the second bending rib height H3B be set to a range in which the height of the extraction liquid is greater than or equal to 50.0% and less than or equal to 70.0%.

As shown in Table 1, the fourth explanatory variable (first bending rib thickness T3A) has a regression coefficient of 0.1700 and the regression coefficient has a p-value of $5.1238 \times 10E-5$ (<0.01), which is the second smallest value. This confirms that the first bending rib thickness T3A affected the sensitivity with a significant level of 1%.

Figure 10:
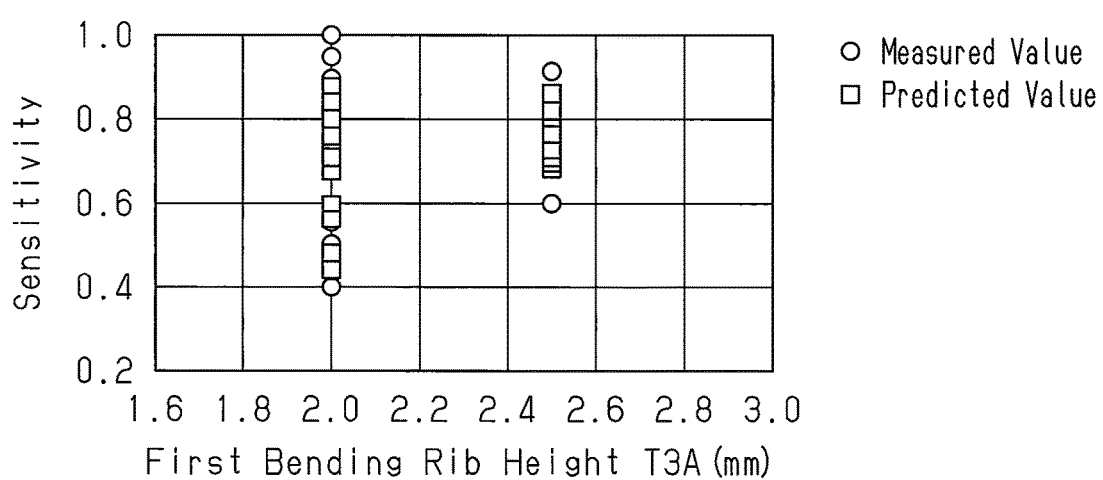
FIG. 10 is a chart showing the result of an experimental example of the relationship of the first bending rib height and the sensitivity.

As shown in FIG. 10, the distribution of a specimen having the first bending rib thickness T3A of 2.5 mm is smaller than the distribution of a specimen having the first bending rib thickness T3A of 2.0 mm. The distribution was 0.02 in forty-five specimens each having the first bending rib thickness T3A of 2.0 mm. The distribution was 0.003 in forty-two specimens each having the first bending rib thickness T3A of 2.5 mm.

When a distribution test was performed based on an F-test, the one-tailed P-value was $1.05 \times 10E-09$ (<0.01), and the significant level was 1%. This confirms that the two types of specimens had different dispersions. That is, this confirms that the dispersion of sensitivity was 0.02 when the first bending rib thickness T3A was 2.0 mm and that the dispersion of sensitivity was 0.003, which is approximately one-tenth of 0.02 and preferable, when the first bending rib thickness T3A was 2.5 mm.

Further, when a test for differences in the average value of the two types of specimens in the distribution was performed, the significant standard was 1%. This confirms that the average value of sensitivity was 0.70 when the first bending rib thickness T3A was 2.0 mm and the average value of sensitivity was 0.75, which is slightly higher than 0.70, when the first bending rib thickness T3A was 2.5 mm. Thus, this confirms that the sensitivity was increased by narrowing the gap between the first bending rib 23A and the second bending rib 23B and by squeezing the extraction subject EM.

As described above, the above embodiment has the following advantages.

(1) When the tubular container 10 is bent, the extraction subject EM is bent and squeezed. Thus, the specimen extraction efficiency increases as compared to a structure that just squeezes the extraction subject EM between fingers or the like and does not bend the tubular container.

(2) The tubular container 10 that is gradually tapered toward the lower side is bent at the lower side of the tubular container 10. This decreases the load necessary to bend the tubular container 10 as compared with when the tubular container 10 is bent at the upper side of the tubular container 10.

(3) The bending width HC is less than the sum of the container thickness T and the extraction subject thickness P. Thus, the extraction subject EM is efficiently squeezed.

(4) The position of the tubular container 10 relative to the two holding portions 21 is always the same in the circumferential direction of the tubular container 10 each time the tubular container 10 is inserted into the holding member 20. This reduces differences in extraction results caused by differences in the position of the tubular container 10 relative to the two holding portions 21 each time the tubular container 10 is inserted into the holding member 20.

(5) The position of the tubular container 10 relative to the two holding portions 21 in the extending direction of the tubular container 10 is always the same for each tubular container 10. This reduces differences in the extraction results between tubular containers caused by differences in the position of the tubular container 10 relative to the two holding portions 21.

(6) The height of the extraction liquid is substantially equal to the guide rib heights H4A and H4B. Thus, when the tubular container 10 is repeatedly bent, the guide ribs 24A and 24B repeatedly press the circumferential wall of the tubular container 10 and agitate the extraction liquid. As a result, the specimen extraction efficiency further increases.

(7) The contact area between the tubular container 10 and the two holding portions 21 increases as the thickness of the two holding portions 21 increases. As a result, the specimen extraction efficiency further increases.

(8) In the examples of FIGS. 7 and 8, the bending ribs 23A and 23B deform the tubular container 10 in a zigzag manner. For example, the deformed tubular container 10 is alternately folded in and out along the axis of the tubular container 10 (refer to single-dashed line shown in FIGS. 5 and 6). In the example of FIG. 8, the distal end of the bending rib 23A is configured to squeeze the tubular container 10 in cooperation with a non-distal end (for example, basal end) of the bending rib 23B. In each of these structures, the extraction subject EM, which may contain a specimen or to which a specimen may be attached, is immersed in the extraction liquid in the tubular container 10 and deformed in a zigzag manner by the bending ribs 23A and 23B. This increases the efficiency for extracting a specimen from the extraction subject EM into the extraction liquid. When external force applied to the two holding portions 21 is released and the bending ribs 23A and 23B move away from the tubular container 10, the tubular container 10 may return to its original shape.

The above embodiment may be modified as follows.

The restriction portion 29 only needs to restrict movement of the tubular container 10 in the extending direction by engaging the flange 12. For example, the insertion tube may include a clamp that fastens the flange 12 over the entire circumference of the flange 12. The restriction portion 29 may be omitted. Even in this structure, advantages (1) to (4), (6), and (7) are obtained. In addition, the tubular container 10 and the holding member 20 will each have a simpler structure than when the restriction portion 29 is provided.

The guide width WG may be greater than the first container width W1 and only needs to be less than the maximum value of the width of the tubular container 10 in the major axis direction DF. Even in such a structure, advantage (4) is obtained. The guide width WG may be greater than the maximum value of the width of the tubular container 10 in the major axis direction DF. In addition, the two guide ribs 24A and 24B may be omitted. In this case, the tubular container may have the shape of a circular tube tapered toward the lower side or may have a tubular shape that bulges at the lower side. Even in such a structure, advantages (1) to (3) and (7) are obtained.

Expression 2 does not need to be satisfied before the two holding portions 21 are moved toward each other and only needs to be satisfied when the two holding portions 21 are moved toward each other. Even in such a structure, advantage (3) is obtained. The bending width HC may be two times greater than the container thickness T over the entire range in which the two holding portions 21 move. Even in such a structure, advantages (1), (2), (4) to (7) are obtained. Further, the extraction subject EM held by the inner surface of the tubular container 10 is bent and squeezed by the inner surface of the tubular container 10. Thus, the specimen extraction efficiency further increases as compared to when the extraction subject EM is just bent.

The portion of tubular container 10 that is bent may be above the middle of the tubular container 10 in the extending direction. In such a structure, since the extraction subject EM accommodated in the tubular container 10 is bent together with the tubular container 10, advantages (1) and (3) to (7) are obtained. Further, in addition to the structure in which the portion of the tubular container 10 that is bent below the middle of the tubular container in the extending direction of the tubular container 10, the range of the position in which the bending ribs are arranged is extended. Consequently, the range in which the extraction subject EM is applied to the specimen extraction kit is extended.

Figure 11:
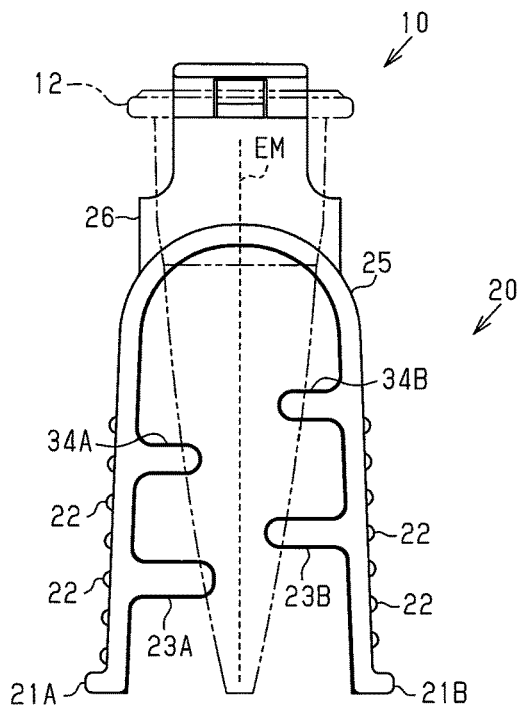
FIG. 11 is a side view showing the holding member of a first modified example.

As shown in FIG. 11, the first holding portion 21A may include the bending rib 23A and a holding rib 34A, and the second holding portion 21B may include the bending rib 23B and a holding rib 34B. In this case, the width between the two bending ribs 34A and 34B in the extending direction may be equal to or different from the bending width HC. In such a structure, advantage (6) is obtained. In addition, since the number of bending portions of the tubular container 10 increases, the specimen extraction efficiency further increases.

Figure 12:
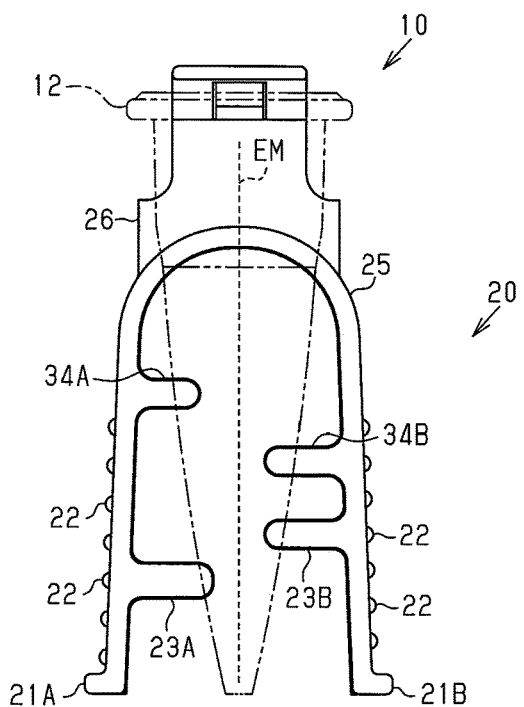
FIG. 12 is a side view showing the holding member of a second modified example.

As shown in FIG. 12, the two bending ribs 23B and 34B may be located between the two bending ribs 23A and 34A in the extending direction of the tubular container 10. Even in such a structure, advantage (6) is obtained. In addition, since the number of bending portions of the tubular container 10 increases, the specimen extraction efficiency further increases.

Figure 13:
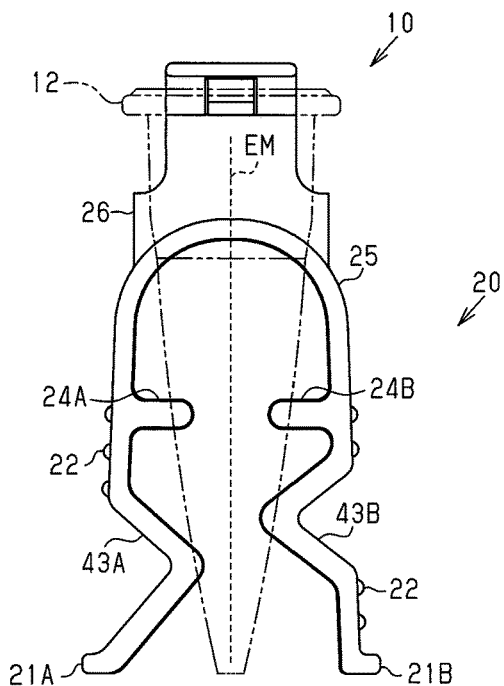
FIG. 13 is a side view showing the holding member of a third modified example.

As shown in FIG. 13, the projection of the first holding portion 21A is not limited to the first bending rib 23A, and the first holding portion 21A may be bent and projected toward the second holding portion 21B so that the bending portion of the first holding portion 21A including an inwardly-directed corner functions as a projection 43A. Further, the projection of the second holding portion 21B is not limited to the second bending rib 23B, and the second holding portion 21B may be bent and projected toward the first holding portion 21A so that the bending portion of the second holding portion 21B including an inwardly-directed corner functions as a projection 43B. In short, the modified example only needs to be configured such that one holding portion includes a projection that projects toward the other holding portion, the two projections are located at different positions in the direction the tubular container 10 extends, and the tubular container 10 is bent when the two holding portions are moved toward each other.

The first bending rib 23A and the second bending rib 23B may be located at the same position in the extending direction. In this structure, the first bending rib 23A and the second bending rib 23B only need to bend the tubular container 10.

Figure 14:
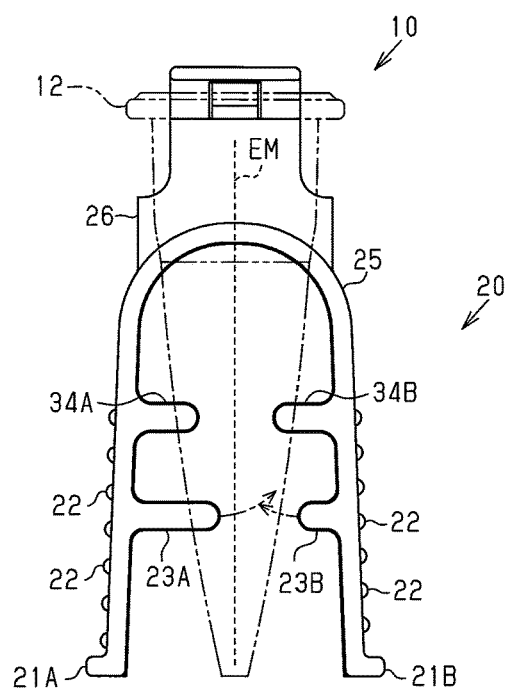
FIG. 14 is a side view showing the holding member of a fourth modified example.

For example, as shown in FIG. 14, the distal end of the first bending rib 23A and the distal end of the second bending rib 23B may be located at opposing positions so that the first bending rib 23A projects more greatly than the second bending rib 23B. Even in such a structure, as shown by the broken line in FIG. 14, the pivot path of the first bending rib 23A is located at the lower side of the pivot path of the second bending rib 23B. Thus, when the first bending rib 23A and the second bending rib 23B are moved toward each other, the tubular container 10 and the extraction subject EM are bent. In addition, when the first bending rib 23A and the second bending rib 23B are further moved toward each other, the tubular container 10 and the extraction subject EM are bent and squeezed.

A structure in which the degree in which the first bending rib 23A presses the tubular container 10 that is set to the holding member 20 differs from the degree in which the second bending rib 23B presses the tubular container 10 as described above may be modified as follows.

Figure 15:
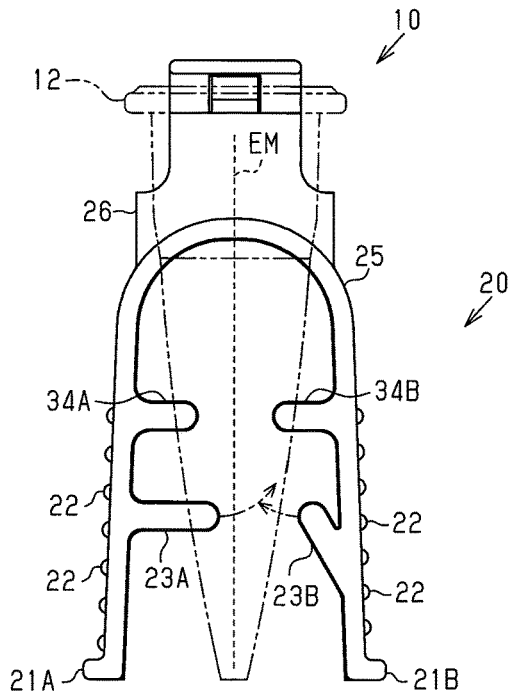
FIG. 15 is a side view showing the holding member of a fifth modified example.

For example, as shown in FIG. 15, the distal end of the first bending rib 23A and the distal end of the second bending rib 23B may be located at opposing positions, and the basal end of the second bending rib 23B may be located at the lower side of the first bending rib 23A. Even in such a structure, as shown by the broken line in FIG. 15, the pivot path of the first bending rib 23A is located at the lower side of the pivot path of the second bending rib 23B.

Figure 16:
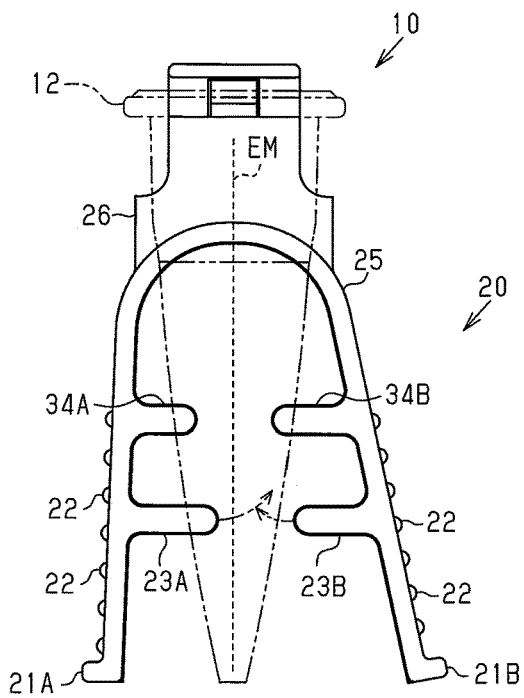
FIG. 16 is a side view showing the holding member of a sixth modified example.

For example, as shown in FIG. 16, the distal end of the first bending rib 23A and the distal end of the second bending rib 23B may be located at opposing positions, and the distance from the second holding portion 21B to the tubular container 10 may be greater than the distance from the first holding portion 21A to the tubular container 10. Even in such a structure, as shown by the broken line in FIG. 16, the pivot path of the first bending rib 23A is located at the lower side of the pivot path of the second bending rib 23B. In the above structure, the tubular container 10 and the extraction subject EM may be squeezed after or when the tubular container 10 and the extraction subject EM are bent.

The bending portion configured to bend the tubular container 10 and the extraction subject EM and the squeezing portion configured to squeeze the tubular container 10 and the extraction subject EM may be located at different positions.

Figure 17:
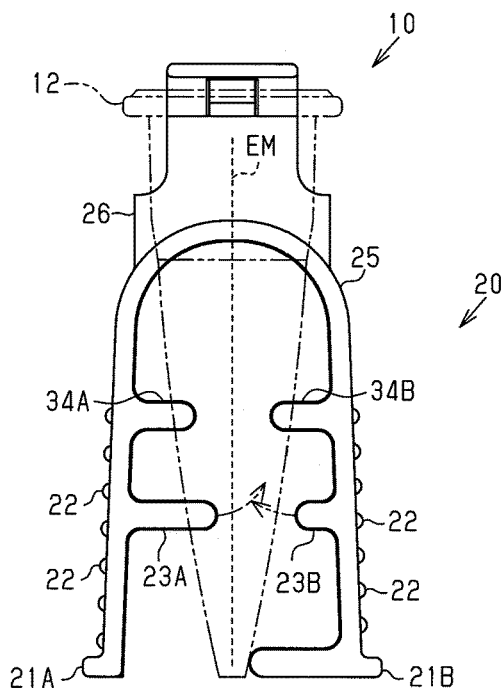
FIG. 17 is a side view showing the holding member of a seventh modified example.

As shown in FIG. 17, the second holding portion 21B includes a further rib that is located at the lower side of the second bending rib 23B and projected toward the first holding portion 21A. The distance from the further rib to the tubular container 10 is shorter than the distance from the second bending rib 23B to the tubular container 10. In such a structure, when the first holding portion 21A and the second holding portion 21B are moved toward each other, the first bending rib 23A bends the tubular container 10 in cooperation with the further rib of the second holding portion 21B. When the first holding portion 21A and the second holding portion 21B are further moved toward each other, the second bending rib 23B functions as the squeezing portion. In such a structure, the bending of the tubular container 10 and the extraction subject EM and the squeezing of the tubular container 10 and the extraction subject EM are performed in different timings. In the above structure, the height of each of the ribs may be set such that the bending of the tubular container 10 and the extraction subject EM is performed at the same time as the squeezing of the tubular container 10 and the extraction subject EM. In addition, the second bending rib 23B may be omitted so that the tubular container 10 and the extraction subject EM are just bent. The tubular container 10 and the extraction subject EM may be just bent using such a specimen extraction kit.

Figure 18:
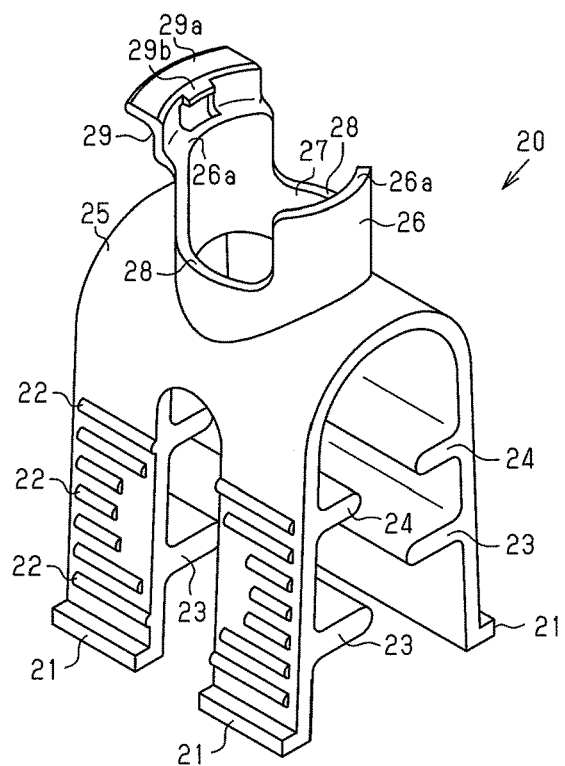
FIG. 18 is a side view showing the holding member of an eighth modified example.

As shown in FIG. 18, a single holding portion 21 may oppose two other holding portions 21. It is only necessary that the holding portions be opposed to one another at opposite sides of the circumferential wall of the tubular container 10 and coupled to one another by an elastically deformable coupling portion.

The shape of each holding portion 21 does not have to be flat and may be curved or square. Alternatively, the two holding portions 21 may have different shapes. In other words, the two holding portions 21 only need to be shaped such that the holding portions 21 are coupled by the coupling portions and located at opposite sides of the circumferential wall of the tubular container.

The plate spring 25 may be a coil spring or a square elastic body. Alternatively, the plate spring 25 may be a member that differs from the two holding portions 21. In other words, the spring 25 only needs to couple the two holding portions 21 so that the two holding portions 21 are elastically deformable to be moved toward each other.

The two holding portions 21 do not have to be pivoted toward each other about the plate spring 25. For example, only a single holding portion 21 may pivot with the plate spring 25 serving as the pivot center. Alternatively, the two holding portions 21 may move toward each other merely in parallel in the holding direction.

The present invention may include the following typical embodiments.

One example of a specimen extraction kit includes a flexible tubular container (10) configured to contain an extraction subject (EM) and an extraction liquid and an elastically deformable holding member (20) configured to receive the tubular container in a manner allowing for removal of the tubular container (10). The holding member (20) includes at least two projections (23A, 23B; 43A, 43B) that deform the tubular container (10), and the at least two projections (23A, 23B; 43A, 43B) are configured to press the tubular container (10) and deform the tubular container (10) in a zigzag manner when the holding member (20) is elastically deformed. For example, the at least two projections (23A, 23B; 43A, 43B) are configured to alternately fold the tubular container (10) in and out along an axis of the tubular container (10).

In some examples, the holding member (20) may include a first holding plate (21A) and a second holding plate (21B) that hold the tubular container (10) in between and a coupling portion (25) that elastically couples the first holding plate (21A) and the second holding plate (21B), and the at least two projections (23A, 23B; 43A, 43B) may include a first projection (23A; 43A) and a second projection (23B; 43B) that project from the first holding plate (21A) and the second holding plate (21B), respectively.

In some examples, a distal end of the first projection (23A) may be configured to partially squeeze the tubular container (10) in cooperation with a non-distal end (for example, basal end) of the second projection (23B).

In some examples, the first projection (23A) and the second projection (23B) may be inwardly-directed projection pieces that project from an inner surface of the first holding plate (21A) and an inner surface of the second holding plate (21B), respectively.

In some examples, the first projection (43A) and the second projection (43B) may include inwardly-directed corners arranged on the first holding plate (21A) and the second holding plate (21B), respectively.

The first projection (23A; 43A) and the second projection (23B; 43B) may be arranged with respect to the axis (single-dashed line in FIGS. 5 and 6) of the tubular container (10) at asymmetrical positions (for example, FIG. 8), with asymmetrical lengths (for example, FIG. 14), at asymmetrical angles (for example, FIG. 15), or with a combination of the asymmetrical positions, the asymmetrical lengths, and the asymmetrical angles. For example, the coupling portion (25) may include a container receiving port (27) that receives the tubular container (10) in a manner allowing for removal of the tubular container (10), and a distance between the first projection (23A; 43A) and the container receiving port (27) may differ from a distance between the second projection (23B; 43B) and the container receiving port (27).

In some examples, the at least two projections (23A, 23B; 43A, 43B) are configured to deform the extraction subject (EM) in a zigzag manner with the extraction subject (EM) immersed in the extraction liquid in the tubular container (10) and a specimen possibly being contained in or attached to the extraction subject (EM).

It should be apparent to those skilled in the art that the present invention may be embodied in other specific forms without departing from the spirit or scope of the invention. For example, the components and/or portions described in the embodiment (or one or a plurality of embodiments) may be partially omitted, and some of the components and/or portions may be combined.

DESCRIPTION OF REFERENCE CHARACTERS

H: Container height
T: Container thickness
DF: Major axis direction
Di: Inner diameter
DV: Minor axis direction
HC: Bending width
W1: First container width
W2: Second container width
W3: Third container width
WG: Guide width
WP: Holding width
H3A: First bending rib height
H3B: Second bending rib height
H4A: First guide rib height
H4B: Second guide rib height
P: Extraction subject thickness
T3A: First bending rib thickness
T3B: Second bending rib thickness
T4A: First guide rib thickness
T4B: Second guide rib thickness
10: Tubular container
11: Container opening
12: Flange
20: Holding member
21: Holding portion
21A: First holding portion
21B: Second holding portion
22: Anti-slip rib
23A: First bending rib
23B: Second bending rib
24A: First guide rib
24B: Second guide rib
25: Plate spring
26: Insertion tube
26*a*: Upper end surface
27: Insertion hole
28: Slot
29: Restriction portion
29*a*: Operation piece
29*b*: Engagement tab
34A, 34B: Bending rib
43A, 43B: Projection

The invention claimed is:

1. A specimen extraction kit comprising:
a flexible tubular container configured to contain an extraction liquid;
an extraction subject accommodated in the tubular container;
holding portions opposed to each other and arranged at opposite sides of a circumferential wall of the tubular container;
an elastically deformable coupling portion that couples the holding portions; and
a bending portion arranged on each of the holding portions, wherein the bending portion is configured to bend the tubular container and the extraction subject.

2. The specimen extraction kit according to claim 1, further comprising a squeezing portion arranged on the opposing holding portions, wherein the squeezing portion squeezes the bent tubular container and the extraction subject.

3. The specimen extraction kit according to claim 1, wherein
the bending portion is a projection that projects from each of the opposing holding portions toward another one of the holding portions, and
the projection bends and squeezes the tubular container and the extraction subject.

4. The specimen extraction kit according to claim 3, wherein
the projections arranged on the opposing holding portions are located at different positions in a direction in which the tubular container extends, and
the projections bend and squeeze the tubular container and the extraction subject when the opposing holding portions are moved toward each other.

5. The specimen extraction kit according to claim 1, wherein
the tubular container includes a portion that is gradually tapered toward a lower end, and
the tubular container is bent and squeezed below a middle of the tubular container in the direction in which the tubular container extends.

6. A specimen extraction kit comprising:
a flexible tubular container configured to contain an extraction subject and an extraction liquid; and
an elastically deformable holding member configured to receive the tubular container in a manner allowing for removal of the tubular container, wherein
the holding member includes at least two projections that deform the tubular container, and the at least two projections are configured to press the tubular container and deform the tubular container in a zigzag manner when the holding member is elastically deformed.

7. The specimen extraction kit according to claim 6, wherein the at least two projections are configured to alternately fold the tubular container in and out along an axis of the tubular container.

8. The specimen extraction kit according to claim 6, wherein
the holding member includes:
a first holding plate and a second holding plate that hold the tubular container in between; and
a coupling portion that elastically couples the first holding plate and the second holding plate, and
the at least two projections include a first projection and a second projection that project from the first holding plate and the second holding plate, respectively.

9. The specimen extraction kit according to claim 8, wherein a distal end of the first projection is configured to partially squeeze the tubular container in cooperation with a non-distal end of the second projection.

10. The specimen extraction kit according to claim 8, wherein the first projection and the second projection are inwardly-directed projection pieces that project from an inner surface of the first holding plate and an inner surface of the second holding plate, respectively.

11. The specimen extraction kit according to claim 8, wherein the first projection and the second projection include inwardly-directed corners arranged on the first holding plate and the second holding plate, respectively.

12. The specimen extraction kit according to claim 8, wherein the first projection and the second projection are arranged with respect to the axis of the tubular container at asymmetrical positions, with asymmetrical lengths, at asymmetrical angles, or with a combination of the asymmetrical positions, the asymmetrical lengths, and the asymmetrical angles.

13. The specimen extraction kit according to claim 12, wherein
the coupling portion includes a container receiving port that receives the tubular container in a manner allowing for removal of the tubular container, and
a distance between the first projection and the container receiving port differs from a distance between the second projection and the container receiving port.

14. The specimen extraction kit according to claim 6, wherein the at least two projections are configured to deform the extraction subject in a zigzag manner with the extraction subject immersed in the extraction liquid in the tubular container and a specimen possibly being contained in or attached to the extraction subject.

15. A method for extracting a specimen, the method comprising holding a flexible tubular container, which is configured to contain an extraction liquid, and an extraction subject, which is accommodated in the tubular container, with opposing holding portions to bend the tubular container and the extraction subject and extract a specimen from the extraction subject.

* * * * *